(12) United States Patent
Taylor (10) Patent No.: US 11,425,982 B1
(45) Date of Patent: Aug. 30, 2022

(54) INTERACTIVE TABLET AND INTEGRATED FACIAL TREATMENT DEVICE

(71) Applicant: Fierra Taylor, Los Angeles, CA (US)

(72) Inventor: Fierra Taylor, Los Angeles, CA (US)

( * ) Notice: Subject to any disclaimer, the term of this patent is extended or adjusted under 35 U.S.C. 154(b) by 0 days.

(21) Appl. No.: 17/495,603

(22) Filed: Oct. 6, 2021

Related U.S. Application Data (60) Provisional application No. 63/144,534, filed on Feb. 2, 2021.

(51) Int. Cl.
| | | |
|---|---|---|
| *A61M 35/00* | (2006.01) | |
| *A61H 33/12* | (2006.01) | |
| *A45D 34/04* | (2006.01) | |
| *A45D 44/00* | (2006.01) | |
| *A45D 34/00* | (2006.01) | |

(52) U.S. Cl.
CPC ........... *A45D 34/04* (2013.01); *A45D 44/005* (2013.01); *A61H 33/12* (2013.01); *A61M 35/00* (2013.01); *A45D 2034/002* (2013.01); *A45D 2034/005* (2013.01); *A45D 2200/057* (2013.01); *A45D 2200/155* (2013.01)

(58) Field of Classification Search
CPC ....... A61H 33/12; A61M 35/00; A45D 34/04; A45D 2034/005; A45D 2200/057; A45D 2200/155
See application file for complete search history.

(56) References Cited

U.S. PATENT DOCUMENTS

| | | | |
|---|---|---|---|
| 4,232,334 A | 11/1980 | Dyson | |
| 6,842,918 B2 * | 1/2005 | Fung | A61H 33/12 4/537 |
| 7,351,215 B1 * | 4/2008 | Roberts | A45D 33/24 132/294 |
| 8,967,400 B1 | 3/2015 | Mumford et al. | |
| 2007/0144455 A1 * | 6/2007 | Ross | A61M 16/101 122/38 |

(Continued)

FOREIGN PATENT DOCUMENTS

| | | |
|---|---|---|
| CN | 103547186 A1 | 1/2014 |
| WO | WO2012015416 A1 | 2/2012 |

OTHER PUBLICATIONS

"Nano Facial Mister, Portable Mini Cool Mist Facial Steamer, USB Rechargeable Mist Handy Sprayer Face Moisturizing & Hydrating for Skin Care," p. 1, publication date unknown <retrieved on Oct. 5, 2021 from: https://www.amazon.co.uk/Portable-Steamer-Rechargeable-Moisturizing-Hydrating/dp/B08JG7H1WM/ref=sr_1_11?dchild=1&keywords=Portable+Mister&qid=1623166324&sr=8-11>.

*Primary Examiner* — Jessica R Arble
(74) *Attorney, Agent, or Firm* — Law Office of Sam Sokhansanj PLLC (57) ABSTRACT

An interactive health, beauty, wellness, and lifestyle tablet device and steamer having a housing and a water basin coupled to the housing. The device can further include a fluid atomizer coupled to the housing, configured to atomize fluid from the water basin, and an interactive display coupled to the housing. Here, the interactive display is configured to receive input from a user. In addition, the housing can also include a lighting unit disposed around the interactive display, and also a heating or cooling element disposed therein. The housing of the device may also include a receptacle for receiving a capsule or container and a tube for releasing and dispensing the contents of the capsule or container, among other features.

7 Claims, 7 Drawing Sheets

(56) References Cited

U.S. PATENT DOCUMENTS

| | | |
|---|---|---|
| 2008/0004953 A1 | 1/2008 | Ma et al. |
| 2008/0173325 A1 | 7/2008 | McGarry |
| 2011/0224745 A1 | 9/2011 | Magruder |
| 2012/0273385 A1 | 11/2012 | Lim et al. |
| 2014/0100926 A1 | 4/2014 | McManus et al. |
| 2014/0257175 A1* | 9/2014 | Quisenberry ......... A61M 35/00 604/290 |
| 2015/0250690 A1* | 9/2015 | Saito ....................... A61Q 5/00 132/200 |
| 2016/0331106 A1* | 11/2016 | Khormaei .............. A46B 11/08 |
| 2016/0354559 A1 | 12/2016 | Gavini et al. |
| 2017/0209840 A1* | 7/2017 | Swallow .............. A61M 11/005 |
| 2019/0029921 A1* | 1/2019 | Liang ................... A61H 33/065 |
| 2020/0187560 A1* | 6/2020 | Trzecieski ............ A24F 40/48 |
| 2021/0268246 A1* | 9/2021 | Wright ................. B05B 5/1691 |

\* cited by examiner

INTERACTIVE TABLET AND INTEGRATED FACIAL TREATMENT DEVICE

CROSS REFERENCE TO RELATED APPLICATIONS

This application claims the benefit of U.S. Provisional Application No. 63/144,534 filed on Feb. 2, 2021, which is incorporated herein by reference in its entirety.

BACKGROUND

This section is intended to introduce the reader to aspects of art that may be related to various aspects of the present disclosure described herein, which are described and/or claimed below. This discussion is believed to be helpful in providing the reader with background information to facilitate a better understanding of the various aspects of the present disclosure described herein. Accordingly, it should be understood that these statements are to be read in this light, and not as admissions of prior art.

Currently, there are many tools that consumers, cosmeticians, or estheticians use during facial cleaning or other types of facial work. One of the most popular tools is a facial treatment device for hydration. A facial treatment device for hydration can deliver steam and other forms of liquid to a user's face.

However, most of the conventional facial hydration devices are designed to merely accomplish a single function, such as applying warm water steam to the user's face. Moreover, given the popularity of various tablet and computing devices, many users use such computing devices to schedule their beauty, health, and wellness routines, learn about trending beauty and wellness related methods, and the like. In addition, such devices are used for other unrelated functions as well that are not dedicated to providing interactivity or feedback to a user with respect to beauty or facial treatment devices. There currently does not exist any product on the market that integrates both a facial hydration device and the interactivity of a computing tablet device into one unitary appliance or device that can soften the skin, open pores, improve skin respiration, tone, and texture, among other benefits. Further, there are various health and wellness tracking and managing devices and software on the market, such as monitoring diet, sleep, and medical conditions, among others. However, no device exists that can combine health and wellness related features in combination with a facial treatment device.

Hence, what is needed is a single unitary combined facial hydrator and integrated tablet device that can also including functionality for lifestyle, health, beauty, and wellness purposes, and provide a cost-effective, optimal, interactive, engaging, and efficient solution for a user.

BRIEF SUMMARY

In one aspect of the disclosure described herein, an integrated facial treatment device and interactivity of a computing tablet device is disclosed for a unitary appliance or device. In addition, the facial treatment device can deliver skincare ingredients, water, and/or liquid in the form of small, micro or nano sized particles in combination with airflow/oxygen, sound waves and/or vibrations to get beyond the skin's barrier instead of sitting on top of the skin. In addition, the facial treatment device can also operate as a steamer, humidifier, vaporizer, hydrator, mist, oxygenator, atomizer, cryotherapy and aromatherapy device which can disperse aroma or scents throughout a room. The integrated facial treatment device can soften the skin, open pores, improve skin respiration, tone, and texture, among other benefits. In particular, a water compartment feature of the device can provide steam, and a skincare compartment feature can provide skincare related fluids via skincare capsules inserted therein, among other features.

The above summary is not intended to describe each and every disclosed embodiment or every implementation of the disclosure. The Description that follows more particularly exemplifies the various illustrative embodiments.

BRIEF DESCRIPTION OF THE DRAWINGS

The following description should be read with reference to the drawings, in which like elements in different drawings are numbered in like fashion. The drawings, which are not necessarily to scale, depict selected embodiments and are not intended to limit the scope of the disclosure. The disclosure may be more completely understood in consideration of the following detailed description of various embodiments in connection with the accompanying drawings, in which.

DETAILED DESCRIPTION

In the Brief Summary of the present disclosure above and in the Detailed Description of the disclosure described herein, and the claims below, and in the accompanying drawings, reference is made to particular features (including method steps) of the disclosure described herein. It is to be understood that the disclosure of the disclosure described herein in this specification includes all possible combinations of such particular features. For example, where a particular feature is disclosed in the context of a particular aspect or embodiment of the disclosure described herein, or a particular claim, that feature can also be used, to the extent possible, in combination with and/or in the context of other particular aspects and embodiments of the disclosure described herein, and in the disclosure described herein generally.

The embodiments set forth below represent the necessary information to enable those skilled in the art to practice the disclosure described herein and illustrate the best mode of practicing the disclosure described herein. In addition, the disclosure described herein does not require that all the advantageous features and all the advantages need to be incorporated into every embodiment of the disclosure described herein.

In one implementation of the disclosure described herein, a display page may include information residing in the computing device's memory, which may be transmitted from the computing device over a network to a central database center and vice versa. The information may be stored in memory at each of the computing device, a data storage resided at the edge of the network, or on the servers at the central database centers. A computing device or mobile device may receive non-transitory computer readable media, which may contain instructions, logic, data, or code that may be stored in persistent or temporary memory of the mobile device, or may somehow affect or initiate action by a mobile device. Similarly, one or more servers may communicate with one or more mobile devices across a network, and may transmit computer files residing in memory. The network, for example, can include the Internet, wireless communication network, or any other network for connecting one or more mobile devices to one or more servers.

Any discussion of a computing, tablet, or mobile device may also apply to any type of networked device, including but not limited to mobile devices and phones such as cellular phones (e.g., an iPhone®, Android®, Blackberry®, or any "smart phone"), a personal computer, iPad®, server computer, or laptop computer; personal digital assistants (PDAs); a roaming device, such as a network-connected roaming device; a wireless device such as a wireless email device or other device capable of communicating wireless with a computer network; or any other type of network device that may communicate over a network and handle electronic transactions. Any discussion of any mobile device mentioned may also apply to other devices, such as devices including Bluetooth®, near-field communication (NFC), infrared (IR), and Wi-Fi functionality, among others.

Phrases and terms similar to "software", "application", "app", and "firmware" may include any non-transitory computer readable medium storing thereon a program, which when executed by a computer, causes the computer to perform a method, function, or control operation.

Phrases and terms similar "network" may include one or more data links that enable the transport of electronic data between computer systems and/or modules. When information is transferred or provided over a network or another communications connection (either hardwired, wireless, or a combination of hardwired or wireless) to a computer, the computer uses that connection as a computer-readable medium. Thus, by way of example, and not limitation, computer-readable media can also comprise a network or data links which can be used to carry or store desired program code means in the form of computer-executable instructions or data structures and which can be accessed by a general purpose or special purpose computer.

Phrases and terms similar to "portal" or "terminal" may include an intranet page, internet page, locally residing software or application, mobile device graphical user interface, or digital presentation for a user. The portal may also be any graphical user interface for accessing various modules, features, options, and/or attributes of the disclosure described herein. For example, the portal can be a web page accessed with a web browser, mobile device application, or any application or software residing on a computing device.

Figure 1:
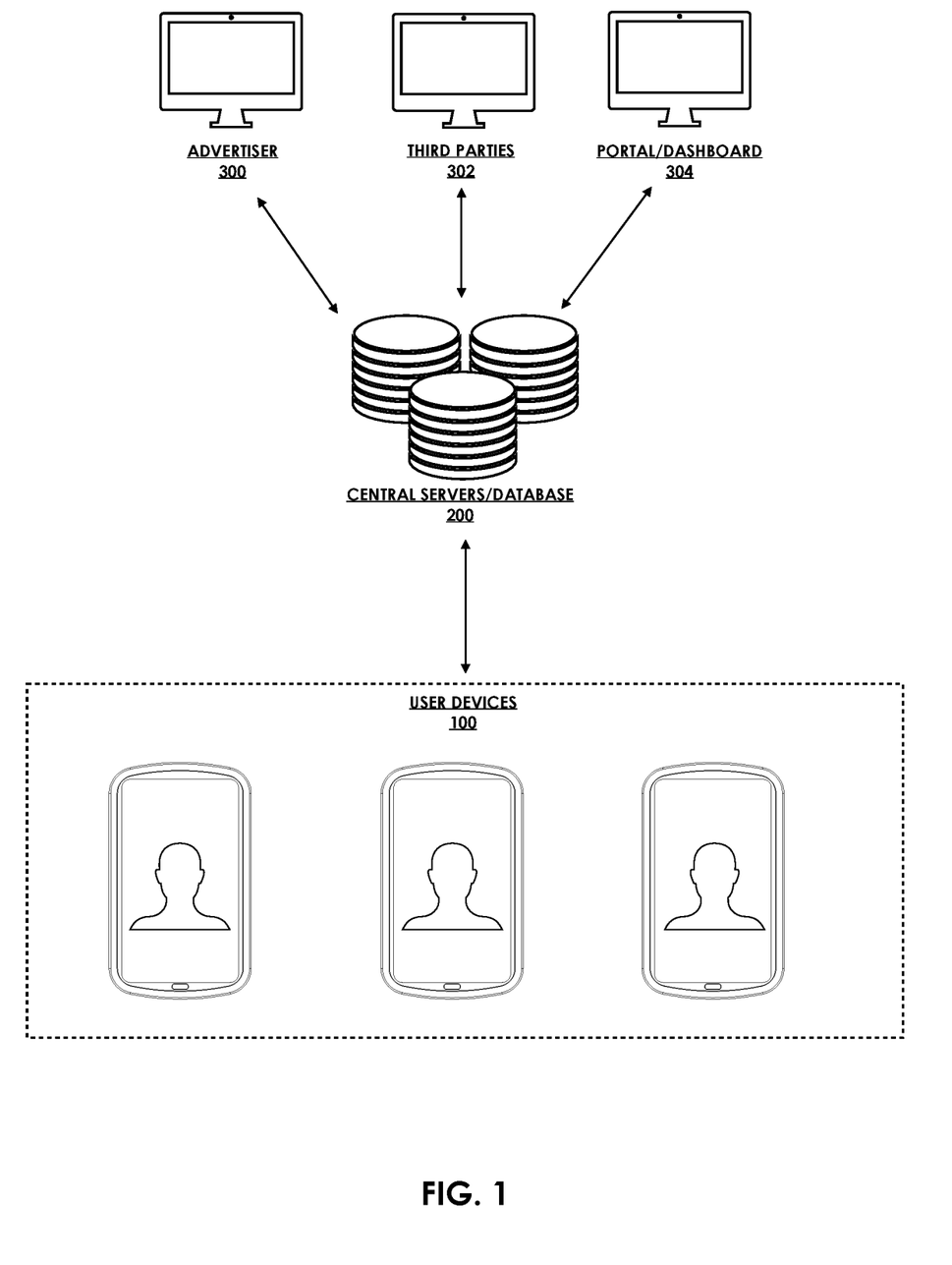
FIG. 1 illustrates an overview block diagram for one non-limiting exemplary embodiment of a network architecture for the interactive lifestyle tablet and facial treatment device of the disclosure described herein.
Figure 2A:
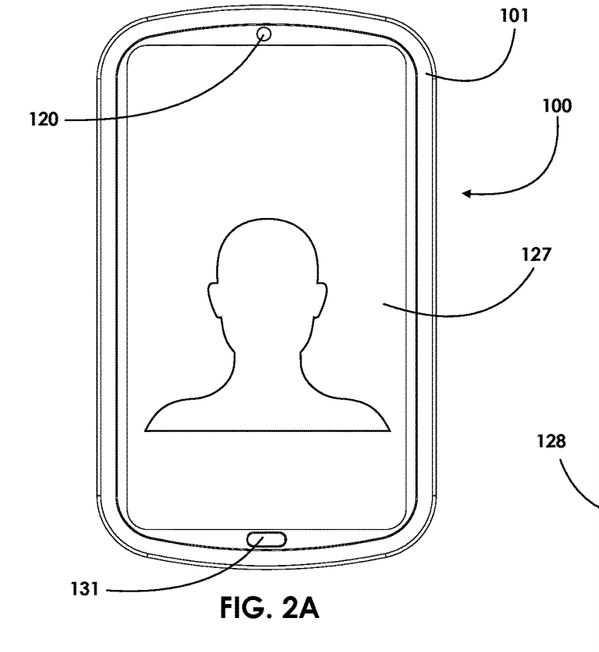
FIG. 2A illustrates a front view for non-limiting exemplary embodiment of the interactive lifestyle tablet and facial treatment device of the disclosure described herein.
Figure 2B:
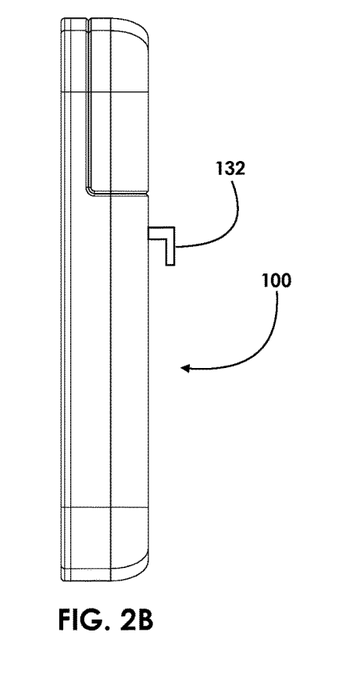
FIG. 2B illustrates a right-side view for the interactive lifestyle tablet and facial treatment device of FIG. 2A.
Figure 2C:
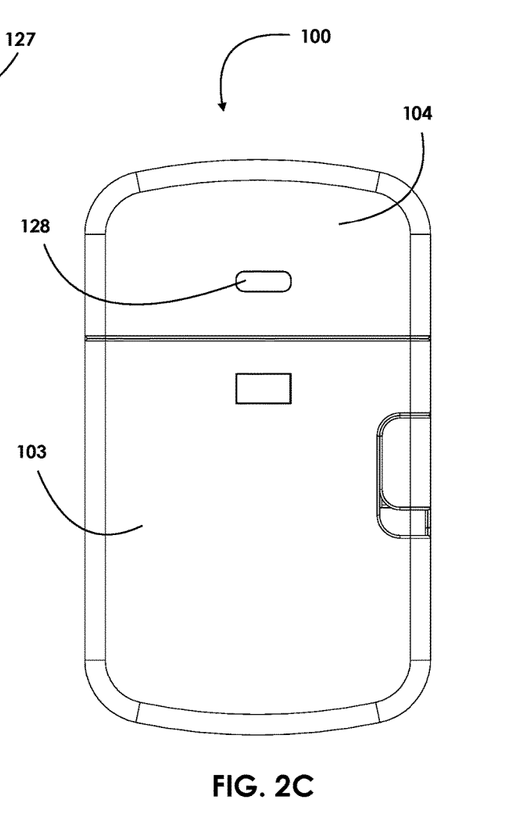
FIG. 2C illustrates a rear view for the interactive lifestyle tablet and facial treatment device of FIG. 2A.
Figure 3:
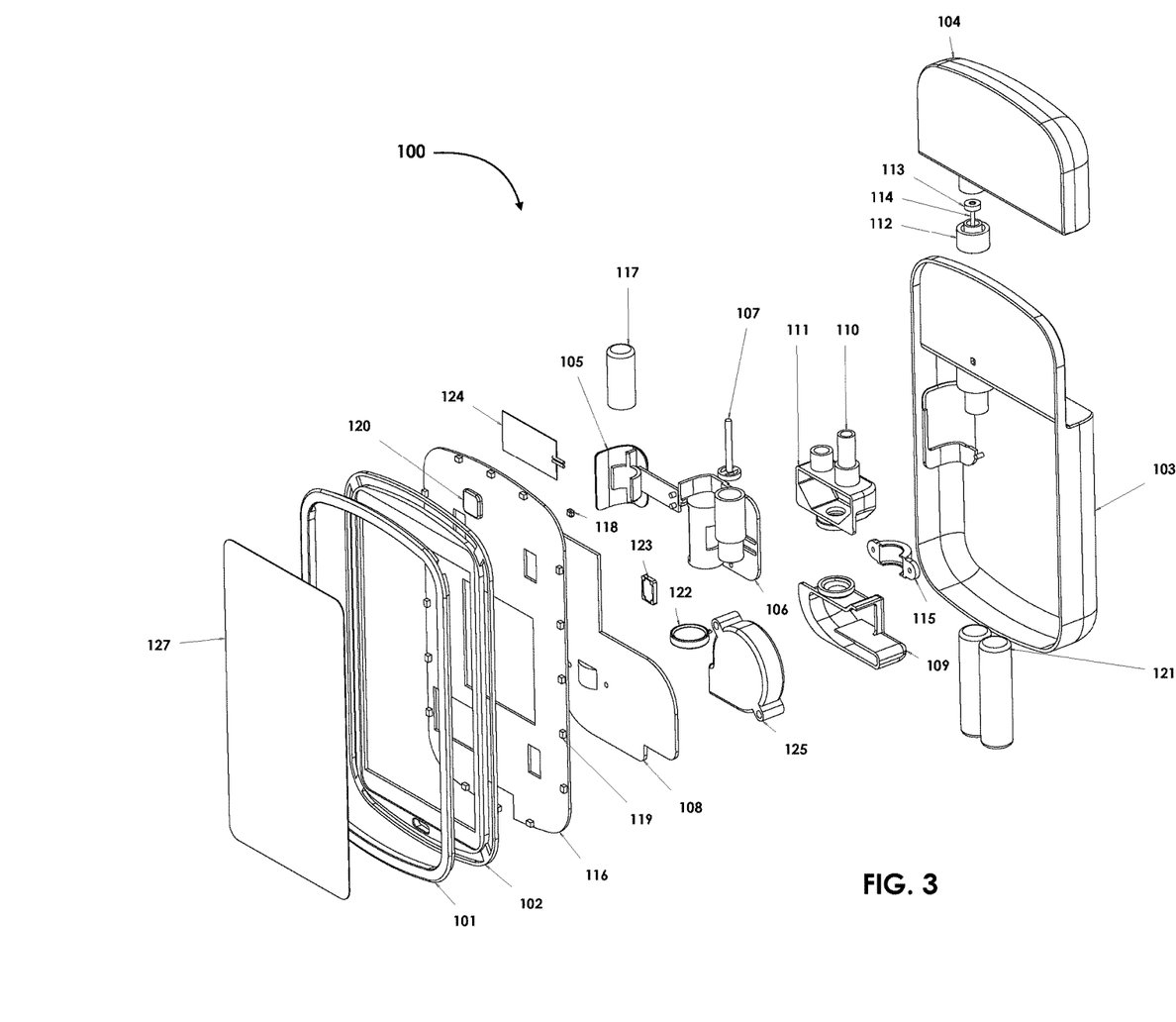
FIG. 3 illustrates a perspective exploded view for the interactive lifestyle tablet and facial treatment device of FIG. 2A.

FIG. 1 illustrates one non-limiting embodiment of a network architecture for the interactive lifestyle, health, wellness, and beauty tablet and facial treatment system and device (IBFT) of the disclosure described herein. Specifically, each IBFT 100 apparatus, via each user device 100, can communicate bi-directionally with one or more central servers/databases 200. In addition, each IBFT 100 may also communicate bi-directionally with each other and share data or be linked to each other, or in the alternative, several IBFT devices may be linked together and collectively send data to servers 200. For example, each IBFT 100 may have integrated voice-enabled hardware and software (with machine learning/AI algorithms), such as Amazon® Alexa, that can allow voice data or information to be sent via each IBFT 100 to servers 200 for interpretation and back to IBS 100 in real-time or near real-time. In the alternative, each IBFT 100 may have its own internal/proprietary machine learning, AI, or neural learning network algorithm.

Still referring to FIG. 1, servers 200 may also communicate bi-directionally and transmit/receive data from advertisers 300, third parties 302, and/or portal/dashboard 304. Specifically, advertisers 300 may receive real time usage/viewing/inventory data from each IBFT 100 and/or transmit audio/visual advertising data to each IBFT 100 depending on such use, and/or create various marketing campaigns targeting various audiences based on age or demographics, among other variables. Further, each IBFT 100 may also integrate with various third-party sources 302, such as via an API, to receive/transmit streaming information, data, programming, content, and any audio/visual data, among others. Further, each IBFT 100 may be integrated with an admin type portal/dashboard with privileges that allows various features in each IBS to be controlled and/or monitored, either locally or wirelessly/remotely.

FIGS. 2A-7C illustrate one non-limiting exemplary embodiment of the IBFT 100 of the disclosure described herein. In particular, referring to FIG. 3, IBFT 100 can include the following: a digital computing device, tablet, and display 127; a lighted strip, lighted LED panel, light diffuser, or light pipe 101; a front panel screen mount 102 for receiving the lighted panel 101; a printed circuit board or controller 116; a digital video camera 120 in communication with controller 116; LED lighting units 119 emitting light through panel 101; a chambered base plate 108; a heater pad or heating or cooling element 124; an ultraviolet or UVC sanitation LED unit 118 in communication with controller 116; a CMS micro speaker or audio output device 123; a piezo disk or piezo atomizer 122; a centrifugal fan 125; a sliding cover capsule holder 105; a switching slider 106, a lower water stopper 107; an atomization chamber 109; a top piezo holder 115; a fluid heat or cooling (chilling or "cryo") chamber 111; a lower water tube 110; a battery power source 121; a rear housing or casing 103; an outer stopper cap 112; a stopper cap plunger 114; a stopper cap bung 113; and a water tank compartment or casing 104. Here, LED lighting units 119 can be used for a variety of purposes and their intensities adjusted, such as for lighting a subject to take high resolution images or video, or for assisting with skin, blood, saliva, stool, or urine analysis captured by the camera. In particular, camera 120 can have various medical diagnostic related features. These diagnostic features can allow camera 120 to detect abnormalities on the skin of a user or within blood, saliva, stool, or urine samples analyzed by the camera (and controller 116) and provide feedback to the user. In addition, device 100 may also include an electrochemical biosensor 128 for analyzing blood, saliva, stool, or urine samples. In addition, the controller 116 of device 100 may also communicate such diagnostic user data to a third party, such as the user's physician for further feedback and analysis. In addition, device 100 may be able to compare images to a repository of images to provide feedback to the user.

Figure 4A:
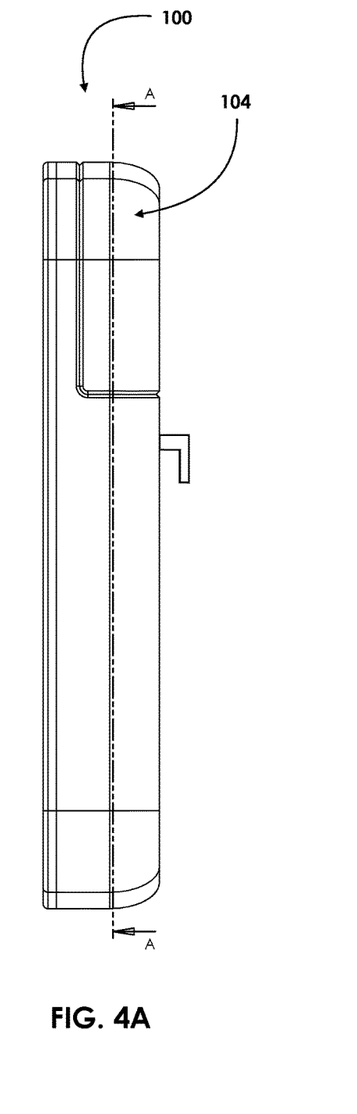
FIG. 4A illustrates another right-side view for the interactive lifestyle tablet and facial treatment device of FIG. 2A.
Figure 4B:
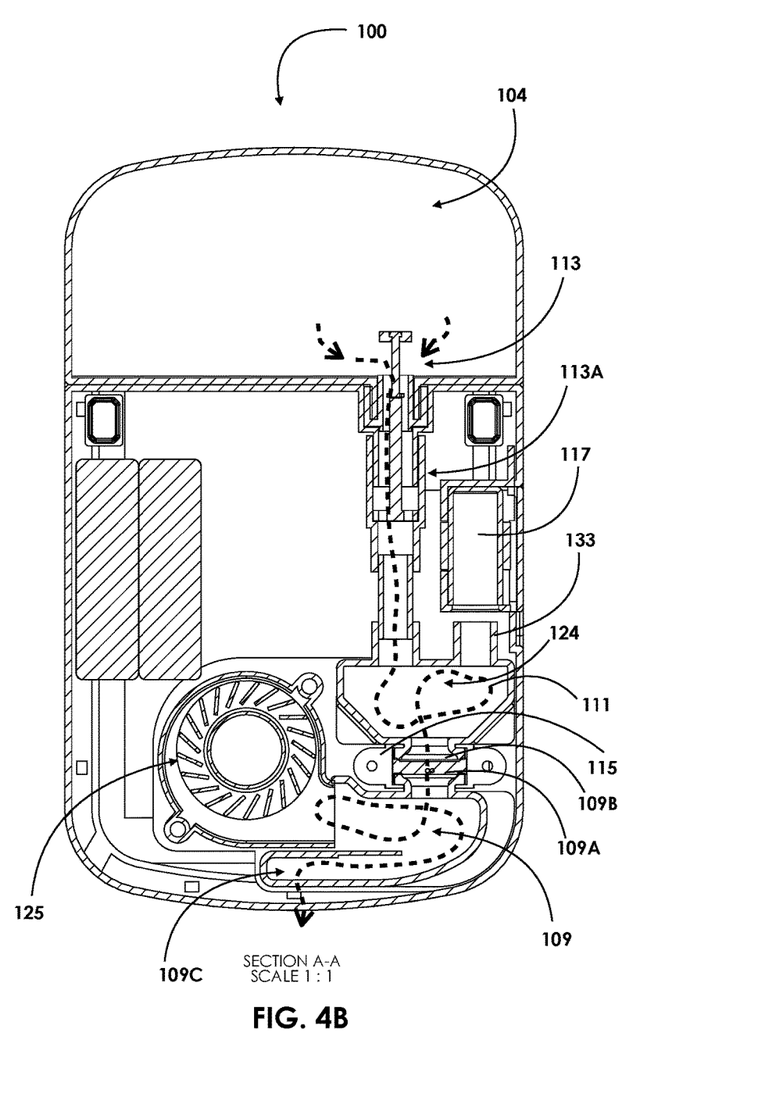
FIG. 4B illustrates a cross-sectional rear view for the interactive lifestyle tablet and facial treatment device of FIG. 2A.
Figure 5A:
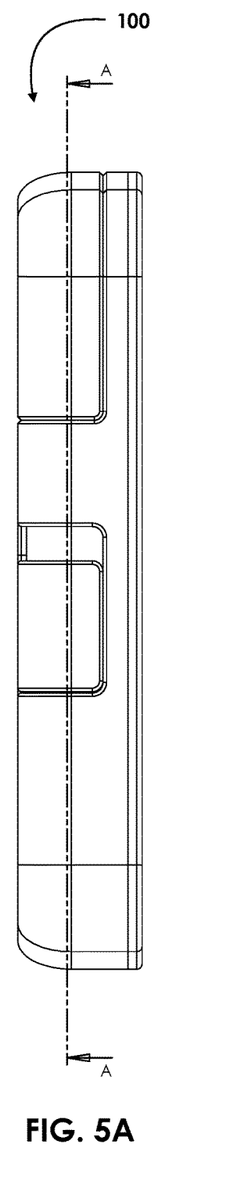
FIG. 5A illustrates a left-side view for the interactive lifestyle tablet and facial treatment device of FIG. 2A.
Figure 5B:
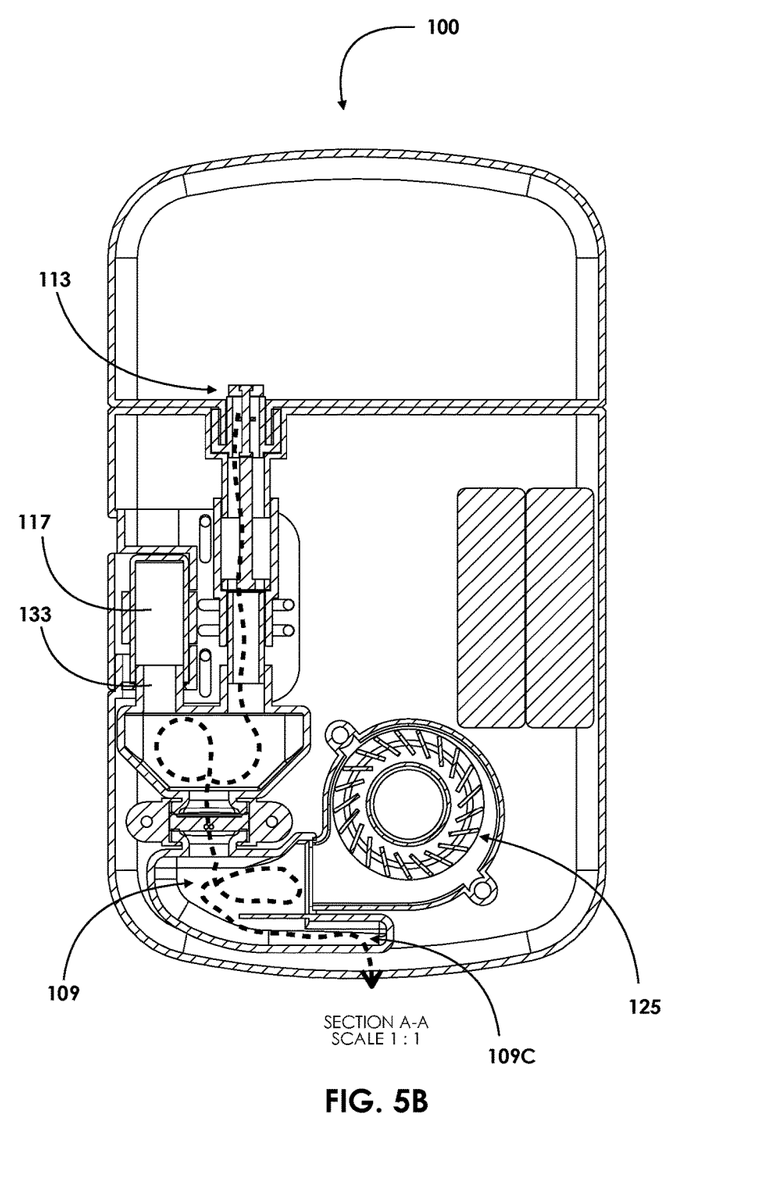
FIG. 5B illustrates a cross-sectional front view for the interactive lifestyle tablet and facial treatment device of FIG. 2A.
Figure 6A:
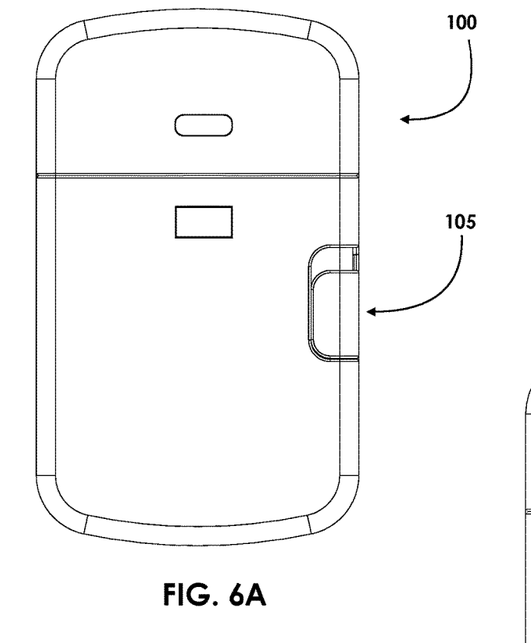
FIGS. 6A-6C illustrates rear views for the interactive lifestyle tablet and facial treatment device of FIG. 2A, further illustrating one non-limiting exemplary embodiment of a method of operation for a capsule door.
Figure 6B:
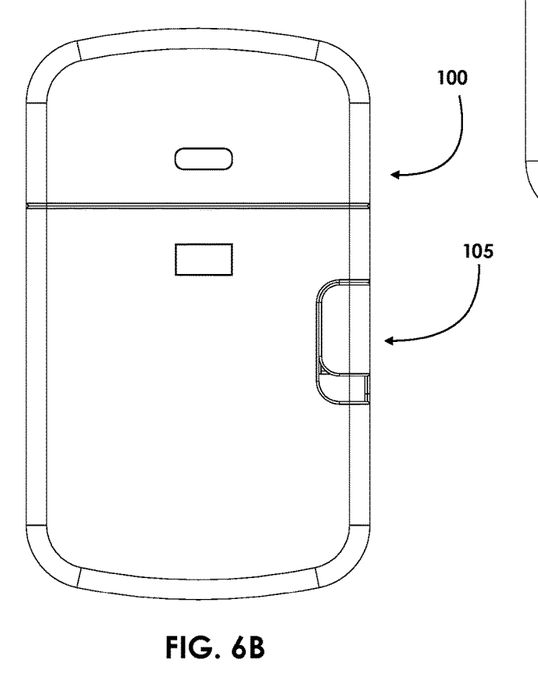
Figure 6C:
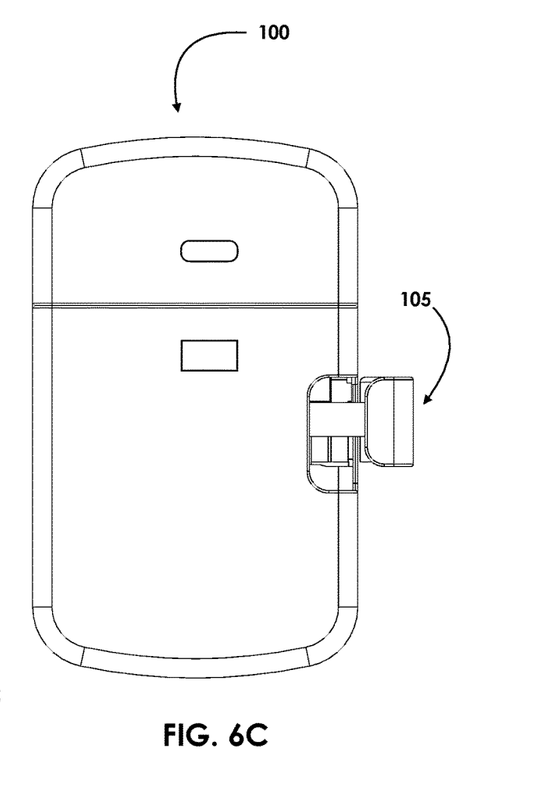
Figure 7A:
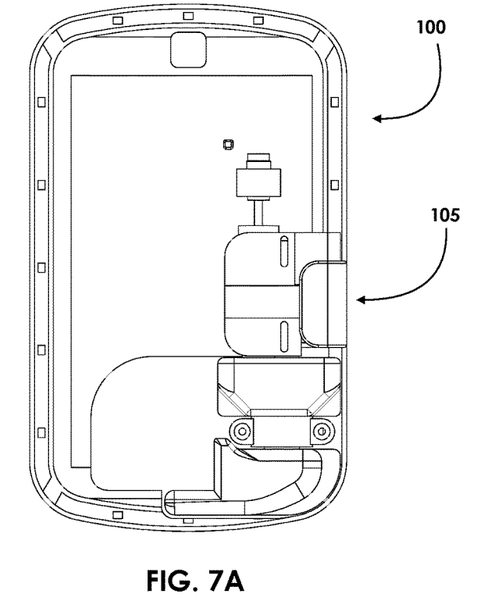
FIGS. 7A-7C further illustrate partial cross-sectional rear views for the interactive lifestyle tablet and facial treatment device of FIGS. 6A-6C.
Figure 7B:
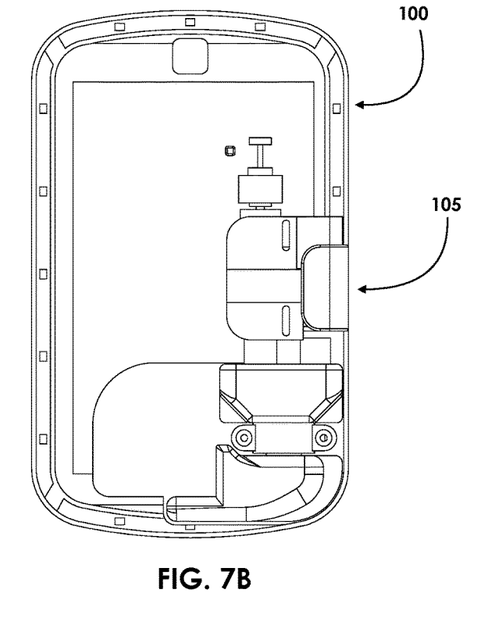
Figure 7C:
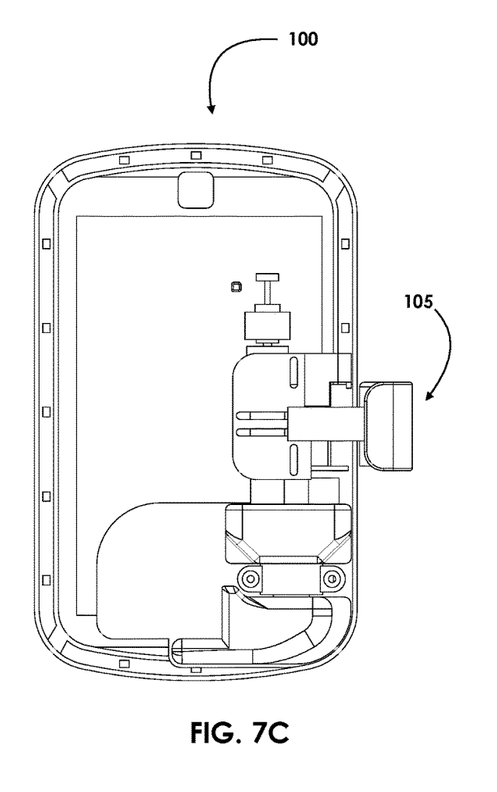

Referring to FIGS. 4B and 5B, in one method of operation, the user can initiate a facial treatment procedure via the interactive display tablet or computing device 127 which sends commands to and from controller 16. In particular, as shown in FIG. 4B, controller 116 can then transmit a signal to one or more electro-motors or solenoid valves within device 100, wherein stopper assembly 112-114 is lifted to allow water or fluids from within tank 104 to be directed downwards, wherein stopper carrier 113A is further lifted, and water is directed to the heating or cooling (chilling or "cryo") chamber 111, as shown in FIG. 4B. Here, the device 100 can automatically determine the amount of water or fluid to disperse from the tank, or in the alternative, the user can configure or define the water or fluid amount. Once the appropriate amount of water is dispensed, the stopper assembly 112-114 can move to its closed position, as shown in FIG. 5B. Once the water or fluid reaches the heating or cooling chamber 111, it is heated or cooled (or chilled) to a pre-defined temperature via heating or cooling element 124. Afterwards, the heated or cooled (or chilled) water is atomized via piezo elements or atomizers 109A and 109B within the piezo holder unit 115. Next the atomized fluid or mist is then directed via a centrifugal fan 125 to atomized fluid chamber 109, which further directs it to area 109C, from which it is then dispensed out of nozzles 131. Here, independent of the heated water operation, one or more fluid based contents within a capsule 117 disposed within capsule holder 105 (wherein a pipe or tube 133 pierces a foil of capsule 117 to release and dispense its contents, as shown in FIG. 5B) can also be dispensed via atomizers 109A and 109B. Once the capsule fluid content is atomized via atomizers 109A and 109B, the atomized capsule fluid can be directed via the centrifugal fan 125 to the atomized fluid chamber 109, which further directs it to area 109C, from which it is then dispensed out of nozzles 131.

Referring to FIGS. 6A-7C, device 100 allows the user to replace capsules 117 with device 100, wherein capsules 117 can be single-use capsules that can be disposed of after their contents are depleted. In another embodiment, capsules 117 may be re-fillable and re-usable. In particular, device 100 includes a hinged or capsule holder 105 that can be lifted into a raised position, such as shown in FIG. 6B, in order to release the capsule 117 within holder 105. Next, once holder 105 is in its raised position, then it can be pivoted or rotated outward, thereby exposing the capsule 117 within holder 105. Here, the user can then remove and replace the capsule 117, and insert a new or different capsule in an inverted configuration (e.g., its foil top facing down). Once the new capsule is inserted within holder 105, the user may pivot and close the rotatable holder 105. Next, the user can then secure and engage the capsule by sliding and pressing the holder 105 in a downward direction thereby securing it in place, as shown in FIG. 6B, such that the foil of capsule 117 is pierced via tube 133 to release and dispense its fluid contents. Once capsule 117 is engaged via tube 133, its contents can be dispensed within atomized chamber 109. Here, capsule 117 may be any type of cartridge, such as various aromas, scents, moisturizers, or fluids. In addition, capsules 117 may also include dietary or topical supplements, over the counter drugs, or pharmaceutical drugs, or any other type of medication that can be used for inhalation or topical application purposes. For example, an application on tablet 127 of device 100 may provide the user the ability to manage and schedule drug administration via device 100, including but not limited to dosage amounts, reminders, etc. In addition, device 100 may also communicate with any type of health care provider over a network to provide real time information such as drug dosage and administration history, and other related patient information. For example, tablet 127 may operate as a portal that allows the user to communicate with his/her healthcare provider such as video/audio while also having drugs administered. Further, capsules 117 can be configured such that they provide a certain amount of dosage of a drug, such as a 30-90 day supply. Alternatively, each capsule may be one dose of a drug.

Referring to FIGS. 2A-5B, IBFT or device 100 may include a casing or housing 104 that functions as a fluid or water basin or reservoir for storing fluid or water therein for distributing within the housing to be heated, atomized and dispense from device 100. Moreover, housing 103 may also include a one-way or two-way valve or port, such as stopper assembly 112, 113, and 114, for allowing fresh water or fluids to be dispersed within device 100. In the alternative, assembly 112, 113, and 114 may also function as a drain port. Further, device 100 also includes a digital interactive tablet or computing device 127 and controller 116 integrated or secured within device 100. In particular, tablet device 127 can be a touch screen digital display device having audio, video, and telecommunications capability, such as an Amazon® Fire, iPad®, or Samsung® Galaxy Tab device. The tablet device 104 may come in various display sizes, including an about 7-inch touch display. In addition, tablet 127 may be heat-resistant, water-proof, or water-resistant. Further tablet 127 may also include an integrated digital image/video camera and audio capturing device 120. Further tablet 127 may also include various sensors, integrated within part 127, that can detect motion, proximity of a user relative to the tablet, and further provide facial recognition capabilities. For example, in one method of operation, tablet 127 can automatically start-up and operate the facial treatment device 100 upon detecting a user in front of it or in certain distance or proximity to it, such as within about two feet. Tablet 127 may also turn off or automatically stop operating the facial treatment device 100 upon detecting that the user has moved away from the tablet beyond a pre-defined distance threshold.

Still referring to FIGS. 2A-5B, device 100 may also include lighting assembly 101 and 119, such as LED lighting disposed around the perimeter or outer ring of device 100 and tablet 127. Here, the intensity, saturation, and color of lighting assembly 101 and 119 can be adjusted via an application residing on tablet 127. Similarly, lighting assembly 101 and 119 may also automatically adjust its intensity based on motion, proximity, and facial recognition sensors 120 of tablet 127, in addition to voice commands from the user. Here, it is further contemplated within the scope of the present disclosure described herein that the front surface of tablet display 127 may include a reflective mirror or reflective surface. In addition, the tablet display 127 may also include a mirror like frame around it.

Still referring to FIGS. 2A-5B, device 100 also includes integrated facial hydrating treatment assembly 106-115, 117,

118, 121, 122, 124, and 125, among others. Here, facial treatment device assembly 106-115, 117, 118, 121, 122, 124, and 125 can be capable of delivering steam, mist, skincare ingredients, hydration, cosmetic product, liquid, and/or water into micro or nano sized particles in combination with airflow/oxygen, sound waves and/or vibrations to get beyond the skin's barrier instead of cosmetic product or liquid sitting on top of the skin. In addition, the facial treatment device assembly 106-115, 117, 118, 121, 122, 124, and 125 can also operate as a humidifier, mister, oxygenator, vaporizer, atomizer, and aromatherapy device which can disperse aroma or scents throughout a room. In particular, facial treatment assembly 106-115, 117, 118, 121, 122, 124, and 125 can include one or more rotatable and adjustable nozzles or ports 131 for dispensing or atomizing steam or mist (externally from device 100) which is extracted from within the atomization chamber 109. In addition, device 100 further includes heating element 124 therein to heat the water or fluid to a desired temperature in order to help generate steam or atomized mist. Here, the temperature and operation of the heating element 124 may also be defined, set, controlled, or regulated via tablet 127. In addition, one or more thermocouples or temperature sensors may be disposed within the housing 103 of device 100 to monitor the temperature of the water via the tablet 127. Here, the facial treatment assembly can include centrifugal fan 125 to assist with dispensing the atomized mist from nozzles 131. Further, additional pumps, vacuums, or fans may be used to assist in pulling and directing steam or mist generated out to nozzles 131 and out of housing 102. However, it is contemplated within the scope of the present disclosure described herein that any other components and method of operation may be used, in lieu of or in combination with, the foregoing components and method of operation. Moreover, housing 103 of device 100 may also include one or more integrated hooks 132 on the rear region to allow device 100 to be hung on a wall. In addition to the hooks 132, or in lieu thereof, magnets or various adhesives may also be used. For example, device 100 may also be fitted with one or more releasable suction cups. In addition, a mount can be provided that can include one or more arms (such as four arms) that can extend device 100 away from a wall or structure, such as from one (1) up to 36 inch.

Still referring to FIGS. 2A-5B, housing 103 of device 100 may also include a portable rechargeable battery power source 121, or be operated via direct power (such as via a plug-in power adaptor) for providing power and/or operating as a hub for delivering power and/or transmitting data to one or more components of device 100. In particular, device 100 may operate via a wired power supply wall plug or efficiently via batteries (which may be rechargeable) that last for at least 7-8 hours. Further, housing 103 may also include ports that provide power and a data communication interface, such as USB power and interface, to various external computing devices. Accordingly, such external devices may communicate with tablet 127 via a wired or wireless connection. In addition, device 100 can be configured to work various efficiency modes to conserve power.

Additional features of the disclosed device 100 may include Amazon® Alexa integration (Voice) system or any AI voice recognition system. In addition, the tablet's camera may include a high-resolution image sensor to capture professional studio quality photos, and further provide skincare and/or skin analysis and color indicators for notifications and dialogue with the integrated AI system. In addition, as discussed, the facial treatment assembly may also operate as a humidifier, aromatherapy, atomizer, oxygenator, cryotherapy, or warm/cold mist by voice command or via the tablet's touch screen. For example, a user may be able to control a level or amount of steam, mist, hydration, liquid, aroma, oxygen, humidification, various warm and cold temperature levels, nanoparticles to penetrate deep into the skin from the mist, and UV light from the lighting member 118, among others. In one embodiment, UV lighting member 118 or an additional UV lighting member can be placed within the water basin 104 for sanitizing the water therein. Further, the water basin 104 of device 100 may hold any amount of water or liquid, such as about 70-100 ML. In addition, dispensing nozzles 131 may be adjustable up to 180 degrees in any direction and further extend out to come towards the user's face when in use. In addition, the start-up time for the mist to be ready to be dispensed may be about 10-30 seconds, and further provide consistent even steam/mist flow, prevent water leakage, reduced noise from steam/mist production, temperature regulated to not cause burns, and automatic shut off when water basin or tank is empty. In addition, water basin 104 may be translucent/clear in order to allow the user to easily view the water level therein.

In addition, applications residing on tablet 127 of IBFT 100 may also provide various services to a user, such as telehealth for skincare examinations by skin specialist or dermatologist (transmitting digital images or streaming video via secure system), LED light therapy, cryotherapy, thermotherapy, microcurrent (face toning), and sonic pulsation. In addition, tablet 104 may also provide or send commands or instructions to a 3D printing cosmetic device (not shown) to produce various color variations for lipstick, eyeshadows, foundations, and powders. In addition, tablet device 127 may also provide augmented or virtual reality capability to allow a user to try on certain beauty/cosmetic products via device cameras and see in real-time how such product appear on the user's face, skin, or body. Moreover, the application or software residing on tablet 127 may also be configured to show daily beauty/health/lifestyle/wellness news, video advertisements, reminders/notifications, time, weather, and the like. In particular, tablet 127 may allow a user to view popular or trending makeup or skincare videos, with the ability to capture and save such videos on the device or send videos to another computing device for viewing at a later time. Moreover, tablet 104 may also provide social networking capabilities (such as being linked to user's social media accounts), record instruction videos and allow a user to participate in live classes or instructional sessions with other users or instructors.

In addition, tablet 127 of device 100 may also provide a shopping platform or interface that allows various other users, retailers, manufacturers, influencers, cosmetologists, or beauty/health/wellness/fitness industry professionals to recommend related products to the user and further allow the user to purchase those products from within an application residing on tablet 127. Further, tablet 127 may have the capability to function as an extension to one's mobile device, such as displaying text messages, voicemails, contacts, calendar reminders, make and receive calls, play music, and the like. In addition, tablet 127 may also display day and night skincare routines and allow the user to customize and configure a particular skin care regimen routine or schedule. In particular, skincare routines may vary from what day of the week or month. For example, a user's day-time routine can be different from the user's nighttime routine. In addition, progress with respect to the user's skin care routine may also be tracked and stored within tablet 127. Moreover, the user may be able to also schedule various types of beauty related appointments from within tablet 127 of device 100, such as hair, nail, and facial care appointments. Moreover, device 100's AI or learning algorithm may also be configured to detect how much of a user's beauty product or health supplements are left based on a particular skin care regime or routine or supplement intake routine, such as frequency of use of a particular product. In addition, the foregoing software algorithm may also automatically let the user know of a products expiration (previously scanned or entered into the application of tablet 127) and further allow the user to re-order or replenish the product. In particular, the camera 120 of tablet 127 can allow the user to create an inventory of his or her health, wellness, and beauty products (and dietary supplements) by scanning the barcodes of product via camera 120.

In addition, the AI or machine learning and managing algorithm of device 100 can store and track customer usage to provide history data and further automatically learn the user's habits. For example, the AI engine can learn about the user's skin care regimen, progress, further determine what features or content on tablet 127's application the user likes and dislikes, voice ordering data, how many total hours is the device in default mode per day, among others.

From the foregoing it will be seen that the present disclosure described herein is one well adapted to attain all ends and objectives herein-above set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts described herein, except insofar as such limitations are included in following claims. Further, it will be understood that certain features and sub-combinations are of utility and may be employed without reference to other features and sub-combinations. This is contemplated by and is within the scope of the claims.

What is claimed is:

1. A computing device and steamer, comprising:
   a housing;
   a fluid basin coupled to the housing and disposed at an upper region of the housing;
   a capsule or cartridge holder coupled to the housing, wherein the capsule or cartridge holder is configured to pivot or rotate to an open or closed position;
   a heating or cooling chamber disposed below the fluid basin, wherein the heating or cooling chamber is configured to receive the fluid from the fluid basin and heat or cool the fluid;
   a fluid atomizer coupled to the housing, wherein the fluid atomizer is disposed below the fluid basin and heating or cooling chamber, and wherein the fluid atomizer is configured to atomize the heated or cooled fluid;
   an atomized fluid chamber;
   one or more nozzles, wherein the one or more nozzles are configured to dispense the atomized fluid from the atomized fluid chamber; and
   a display coupled to the housing, wherein the display substantially extends to the length of the housing such that the fluid basin, heating or cooling chamber, fluid atomizer, and the atomized fluid chamber are disposed behind the display.

2. The computing device and steamer of claim 1, wherein the display is configured to receive input from a user.

3. The computing device and steamer of claim 1, wherein the housing further comprises a lighting unit disposed around the display.

4. The computing device and steamer of claim 1, wherein the housing further comprises a heating or cooling element.

5. The computing device and steamer of claim 1, wherein the housing further comprises a centrifugal fan.

6. The computing device and steamer of claim 1, wherein the capsule or cartridge holder is adapted to receive a capsule or container.

7. The computing device and steamer of claim 6, wherein the housing further comprises a tube for releasing and dispensing the contents of the capsule or container.

* * * * *